United States Patent
Katashiba et al.

(10) Patent No.: US 11,134,841 B2
(45) Date of Patent: Oct. 5, 2021

(54) IMAGE ACQUISITION APPARATUS AND METHOD FOR CONTROLLING THE SAME

(71) Applicant: CANON KABUSHIKI KAISHA, Tokyo (JP)

(72) Inventors: Yuji Katashiba, Kawasaki (JP); Kazuhiro Matsumoto, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/796,655

(22) Filed: Feb. 20, 2020

(65) Prior Publication Data

US 2020/0187773 A1  Jun. 18, 2020

Related U.S. Application Data

(63) Continuation of application No. PCT/JP2018/030043, filed on Aug. 10, 2018.

(30) Foreign Application Priority Data

Aug. 28, 2017  (JP) .............................. JP2017-163475

(51) Int. Cl.
*A61B 3/10* (2006.01)
*A61B 3/12* (2006.01)
*G01B 9/02* (2006.01)

(52) U.S. Cl.
CPC ............ *A61B 3/102* (2013.01); *A61B 3/1225* (2013.01); *G01B 9/0203* (2013.01); *G01B 9/02063* (2013.01); *G01B 9/02091* (2013.01)

(58) Field of Classification Search
None
See application file for complete search history.

(56) References Cited

U.S. PATENT DOCUMENTS

2006/0109478 A1* 5/2006 Tearney ............... G01B 9/0205
356/479
2008/0024767 A1  1/2008 Seitz
(Continued)

FOREIGN PATENT DOCUMENTS

| CN | 103222850 A | 7/2013 |
| CN | 104414621 A | 3/2015 |

(Continued)

*Primary Examiner* — Shawn Decenzo
(74) *Attorney, Agent, or Firm* — Canon U.S.A., Inc. IP Division (57) ABSTRACT

An image acquisition apparatus includes a light source configured to emit light, a dividing unit configured to divide the light from the light source into reference light and measurement light, an image forming unit configured to form a tomographic image of a subject based on interfered light in which return light from the subject irradiated with the measurement light and the reference light are interfered, a focus adjusting unit configured to adjust a focus of the measurement light, an optical-path-length adjusting unit configured to adjust an optical path length of the reference light, and a control unit configured to adjust the optical path length of the reference light by controlling the optical-path-length adjusting unit according a change in an optical path length of the measurement light caused by adjustment of the focus using the focus adjusting unit.

10 Claims, 6 Drawing Sheets

(56) References Cited

U.S. PATENT DOCUMENTS

| | | | |
|---|---|---|---|
| 2009/0244547 A1* | 10/2009 | Ozawa | G01B 9/02004 356/511 |
| 2010/0014089 A1* | 1/2010 | Yamada | G01B 9/0203 356/450 |
| 2012/0162660 A1* | 6/2012 | Kemp | G01B 9/02057 356/479 |
| 2012/0189184 A1* | 7/2012 | Matsumoto | A61B 3/102 382/131 |
| 2013/0194541 A1* | 8/2013 | Aoki | G01B 9/02091 351/206 |
| 2013/0242258 A1 | 9/2013 | Higuchi | |
| 2015/0062589 A1 | 3/2015 | Osawa | |
| 2015/0116664 A1* | 4/2015 | Uchida | A61B 3/1025 351/206 |
| 2017/0215725 A1* | 8/2017 | Ishiai | A61B 3/1225 |
| 2018/0017370 A1 | 1/2018 | Yamauchi et al. | |
| 2018/0283846 A1* | 10/2018 | Katashiba | G01B 9/02058 |
| 2018/0289251 A1* | 10/2018 | Matsumoto | A61B 3/14 |
| 2019/0150729 A1* | 5/2019 | Huang | A61B 3/102 |
| 2019/0376781 A1* | 12/2019 | Kato | G01B 9/02063 |
| 2020/0297209 A1* | 9/2020 | Katashiba | A61B 3/102 |

FOREIGN PATENT DOCUMENTS

| | | |
|---|---|---|
| EP | 1887312 A1 | 2/2008 |
| EP | 2620097 A1 | 7/2013 |
| JP | 2004-191114 A | 7/2004 |
| JP | 2013-153798 A | 8/2013 |
| JP | 2015-49204 A | 3/2015 |
| JP | 2015-221091 A | 12/2015 |
| JP | 2016-49368 A | 4/2016 |
| WO | 2016/121249 A1 | 8/2016 |

* cited by examiner

IMAGE ACQUISITION APPARATUS AND METHOD FOR CONTROLLING THE SAME

CROSS-REFERENCE TO RELATED APPLICATIONS

This application is a Continuation of International Patent Application No. PCT/JP2018/030043, filed Aug. 10, 2018, which claims the benefit of Japanese Patent Application No. 2017-163475, filed Aug. 28, 2017, both of which are hereby incorporated by reference herein in their entirety.

TECHNICAL FIELD

The present invention relates to image acquisition apparatuses and, in particular, to an image acquisition apparatus for use in acquiring a tomographic image of, for example, the eye fundus of a subject eye, as well as a method for controlling the same.

BACKGROUND ART

Optical coherence tomography (OCT) using multiwavelength interference is a method for acquiring a high-resolution tomographic image of a specimen (in particular, eye fundus). An apparatus for acquiring a tomographic image using such OCT is hereinafter referred to as an OCT apparatus.

In recent years, it has become possible to acquire a tomographic image of a retina with improved lateral resolution by increasing the beam diameter of measurement light using a Fourier domain OCT apparatus. However, the increase in the beam diameter of the measurement light may decrease the signal-to-noise (SN) ratio and the resolution of the acquired tomographic image of the retina due to the aberration of the subject eye.

To solve the above problem, an adaptive optics OCT apparatus has been developed which includes an adaptive optics system that measures the aberration of the subject eye using a wavefront sensor in real time and that corrects the generated aberration using a wavefront correction device to allow acquiring a tomographic image with high lateral resolution. Apparatuses including the adaptive optics system have the problem of a decrease in aberration measurement accuracy due to unwanted reflected light from the lens surface or the like entering the wavefront sensor.

To prevent such unwanted reflected light, a reflection optical system mainly constituted by mirrors is used. PTL 1 discloses an adaptive optics OCT apparatus that performs focus adjustment on the eye fundus of the subject eye by moving a focus optical system including mirrors disposed in the measurement optical path.

CITATION LIST

Patent Literature

PTL 1 Japanese Patent Laid-Open No. 2015-221091

When focus adjustment is performed by moving the positions of the mirrors in the measurement optical path, the optical path length of the measurement light changes with the focus adjustment. The change in the optical path length of the measurement light cause a change in the display position of the tomographic image because the depthwise display position of the tomographic image depends on the difference in optical path length between the measurement light and the reference light. The display position of the tomographic image can be adjusted by adjusting the optical path length of the reference light by moving the reference mirror. However, when the optical path length of the measurement light changes with the focus adjustment, the procedure of adjustment is complicated because it is impossible to independently adjust only focusing.

Furthermore, the movable range of the reference mirror needs to cope with variations in the axial length of the subject eye and the change in the optical path length of the measurement light due to focus adjustment. For this reason, the movable range needs be large (long) correspondingly. Since the increase in the reference mirror movable range increases the search range at the reference mirror adjustment, the adjustment takes much time.

In contrast, using a wavefront correction device, such as a deformable mirror, allows independently adjusting only focusing without changing the optical path length of the measurement light. However, in this case, the adjustable focus range and the correctable aberration amount are limited because the stroke of the deformable mirror has a limitation.

Accordingly, it has been difficult to acquire high lateral resolution tomographic images of the subject eye which are present over a wide diopter range in a relatively short time.

SUMMARY OF INVENTION

According to an aspect of the present invention, an image acquisition apparatus includes a light source configured to emit light, a dividing unit configured to divide the light from the light source into reference light and measurement light, an image forming unit configured to form a tomographic image of a subject based on interfered light in which return light from the subject irradiated with the measurement light and the reference light are interfered, a focus adjusting unit configured to adjust a focus of the measurement light, an optical-path-length adjusting unit configured to adjust an optical path length of the reference light, and a control unit configured to adjust the optical path length of the reference light by controlling the optical-path-length adjusting unit according a change in an optical path length of the measurement light caused by adjustment of the focus using the focus adjusting unit.

Further features of the present invention will become apparent from the following description of exemplary embodiments with reference to the attached drawings.

DESCRIPTION OF EMBODIMENTS

Embodiments of the present invention will be described. An example of images acquired by the apparatus of the present embodiments is a tomographic image of the retina of the human eye. It is to be understood that the following embodiments are not intended to limit the present invention according to the claims and that not all combinations of the features described in the embodiments are essential for the solution of the present invention.

First Embodiment

A first embodiment of the present invention will be described in detail hereinbelow with reference to the drawings.

Apparatus Configuration

Figure 1:
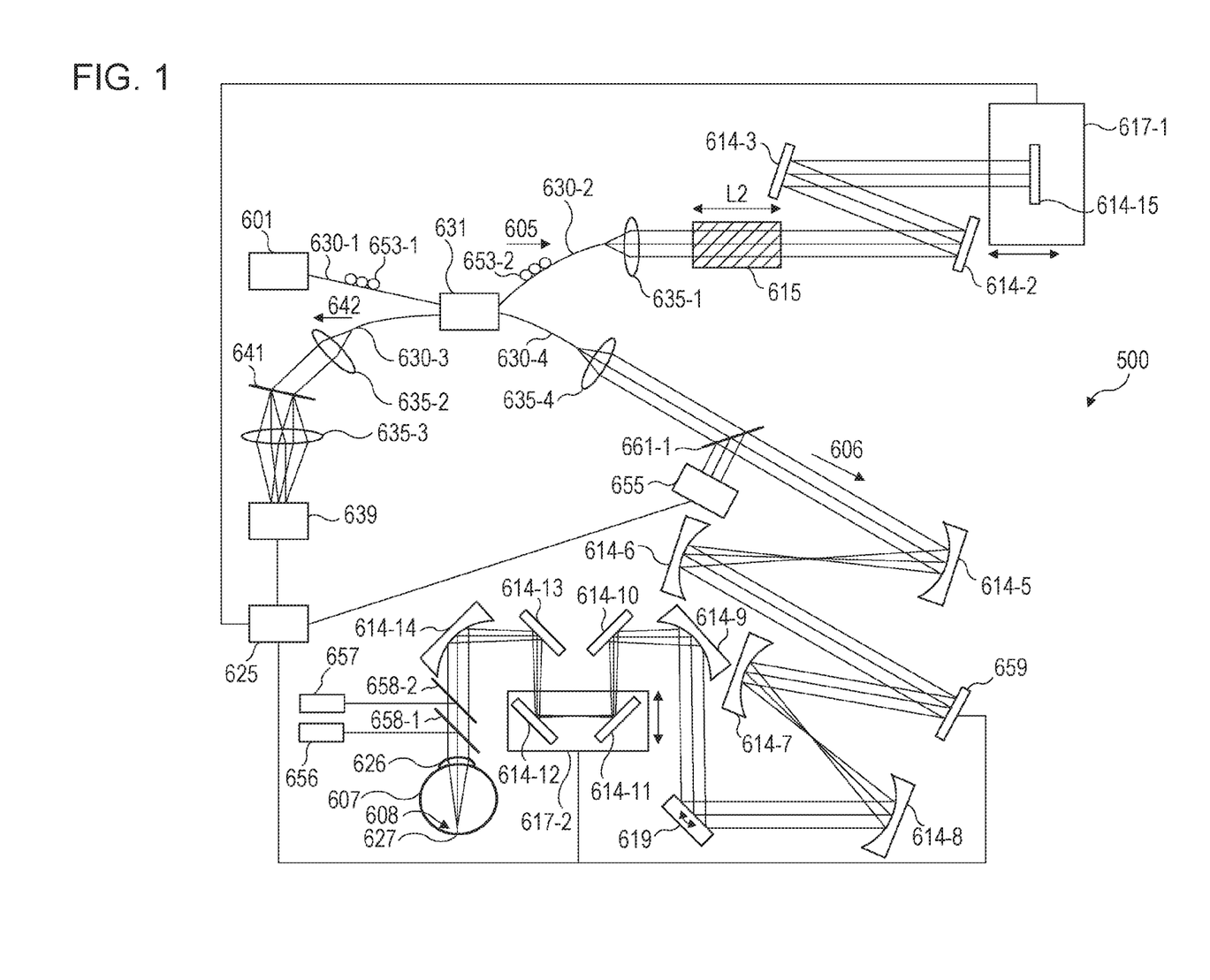
FIG. 1 is a schematic diagram illustrating the configuration of a tomographic-image acquisition system according to a first embodiment of the present invention.

A tomographic-image acquisition system 500, which is a form of an optical interference tomographic-image acquisition system according to the present embodiment, will be described with reference to FIG. 1. In the present embodiment, the entire optical system is constituted by a reflection optical system mainly using a plurality of mirrors, or reflection members.

A light source 601 in the present embodiment is a light source for emitting light (low coherence light) for irradiating a subject eye 607, which is an object to be examined. The light source 601 is a super luminescent diode (SLD) having a center wavelength of 830 nm and a band width of 50 nm. Although the SLD is selected as the light source, any light source that emits low coherence light may be used. For example, amplified spontaneous emission (ASE) may be used. Near infrared wavelengths are suitable in consideration of measuring the eye. The wavelength is preferably as short as possible, here 830 nm because the wavelength influences the lateral resolution of the acquired tomographic image. Depending on the measurement region to be observed, a different wavelength may be selected. The wider the wavelength band, the higher the resolution in the depth direction. In general, with a center wavelength of 830 nm, a resolution of 6 μm is obtained at the 50 nm band width, and a resolution of 3 μm is obtained at the 100 nm band width.

Light emitted from the light source 601 passes through a single mode fiber 630-1 into an optical coupler 631, which is a dividing unit in the present embodiment, where the light is divided at an intensity ratio of 90 to 10 into reference light 605 and measurement light 606. The separation ratio is not limited to the above ratio but is selected as appropriate according to the object to be examined.

Next, the optical path of the reference light 605 will be described. The reference light 605 obtained by dividing the light with the optical coupler 631 passes through a single mode fiber 630-2 into a lens 635-1, where the reference light 605 is adjusted to parallel light with a beam diameter of 2 mm. Next, the reference light 605 is guided to a mirror 614-15 serving as a reference mirror by mirrors 614-2 to 614-3. Here, a flat mirror is used as the reference mirror. The light reflected by the mirror 614-15 is again reflected by the mirror 614-3 and the mirror 614-2 in sequence into the optical coupler 631.

A dispersion compensation glass 615 through which the reference light 605 passes is used to compensate the dispersion of the measurement light 606 traveling between a lens 635-4 and the subject eye 607 to be examined for the reference light 605. The length of the dispersion compensation glass 615 is L2 (here, L2=20 mm).

The mirror 614-15 is mounted on an electrically driven stage 617-1 and constitutes an optical-path-length adjusting unit in the present embodiment. The electrically driven stage 617-1 can move in the direction indicated by the arrow to adjust and control the optical path length of the reference light 605. Here, the movable range of the electrically driven stage 617-1 is set at 350 mm. The electrically driven stage 617-1 is controlled by a personal computer 625, which is a control unit in the present embodiment.

Next, the optical path of the measurement light 606 will be described. The measurement light 606 obtained by dividing the light with the optical coupler 631 passes through a single mode fiber 630-4 into the lens 635-4, where the measurement light 606 is adjusted to parallel light with a beam diameter of 4 mm.

Next, the measurement light 606 passes through a beam splitter 661-1 and is reflected by mirrors 614-5 to 614-6 onto a deformable mirror 659. The deformable mirror 659 is a mirror device that corrects the aberration between the measurement light 606 and return light 608 by deforming the mirror shape flexibly based on the aberration detected by a wavefront sensor 655. Although the deformable mirror is used as the wavefront correction device, any device that corrects the aberration may be used, for example, a spatial-light-phase modulator using a liquid crystal may be used.

Next, the measurement light 606 is reflected by mirrors 614-7 to 614-8 onto the mirror of an X-Y scanner 619. Although the X-Y scanner 619 here includes one mirror for the sake of clarity, the X-Y scanner 619 actually includes two mirrors for X scanning and Y scanning disposed close to each other and raster-scans a retina 627 in a direction perpendicular to the optical axis. The measurement light 606 is adjusted so that the center is aligned with the rotation center of the mirrors of the X-Y scanner 619. The configuration of the X-Y scanner 619 is not limited to the above configuration. An optical system may be disposed between the two mirrors of the X-Y scanner 619, in which mirrors are disposed at the conjugate positions of the pupil 626.

Mirrors 614-9 to 614-14 constitute an optical system for scanning the retina 627 at the eye fundus of the subject eye 607 and has the role of scanning the retina 627 with the measurement light 606, with the vicinity of the pupil 626 as the fulcrum.

The mirrors 614-11 and 614-12 are mounted as a set of reflection members on an electrically driven stage 617-2 and constitute a focus adjusting unit in the present embodiment. The electrically driven stage 617-2 can move in the direction indicated by the arrow to adjust the focus of the measurement light 606. This allows coping with the diopter of the subject eye 607. Here, the movable range of the electrically driven stage 617-2 is set at 160 mm.

The electrically driven stage 617-2 can be controlled by the personal computer 625 which is the control unit of the present embodiment.

Thus, the single mode fiber 630-4 to the mirror 614-14 constitute a measurement optical system in the present embodiment.

When the measurement light 606 is incident on the subject eye 607, the measurement light 606 is reflected and scattered from the retina 627 into the return light 608 and is guided to the optical coupler 631 again. The reference light 605 described above and the return light 608 are interfered by the optical coupler 631 and is divided from each other at a ratio of 90 to 10. The obtained interfered light 642 passes through a single mode fiber 630-3 and a lens 635-2 and is separated by a transmission grating 641 for each wavelength. The interfered light 642 is collected by a lens 635-3 and is then converted to a voltage by a line camera 639 for each position (wavelength).

Specifically, interference fringes of the spectral region on the wavelength axis is observed on the line camera 639. The obtained voltage signals are converted to digital values, which are processed by the personal computer 625 serving as an image forming unit in the present embodiment to form a tomographic image. The range of the tomographic images formed in the depth direction depends on the relationship (wavelength resolution) between the interference fringes and the number of pixels of the line camera 639 that receives the light. Here, the number of pixels of the line camera 639 is set at 1,000, and the tomographic-image acquisition range is set at 2 mm. The formed tomographic images are displayed on the monitor (not illustrated), which is a display unit in the present embodiment of the personal computer 625, by the personal computer 625 serving as a display control unit in the present embodiment.

Part of the return light 608 produced by the beam splitter 661-1 enters the wavefront sensor 655, where the aberration of the return light 608 is measured. The wavefront sensor 655 used here is a Shack Hartmann wavefront sensor. The wavefront sensor 655 is electrically connected to the personal computer 625. The obtained aberration is expressed using Zernike polynomials by the personal computer 625. This expresses the aberration of the subject eye 607.

The component of defocus of the Zernike polynomials is used to control the positions of the mirrors 614-11 to 614-12 using the electrically driven stage 617-2 to correct the diopter of the subject eye 607. Components other than the component of defocus are used to control and correct the surface shape of the deformable mirror 659, allowing acquisition of tomographic images with hither lateral resolution.

The mirrors 614-5 to 814-14 are disposed so that the pupil 626, the X-Y scanner 619, the wavefront sensor 655, and the deformable mirror 659 are optically conjugate, allowing the wavefront sensor 655 to measure the aberration of the subject eye 607.

Next, an anterior-eye observation optical system will be described. The anterior-eye observation optical system incudes a dichroic mirror 658-1, an anterior-eye observation camera 656, and an anterior-eye illuminating light source (not illustrated). The dichroic mirror 658-1 reflects infrared light from the anterior-eye illuminating light source and transmits the measurement light 606 and the return light 608. The optical axis of the anterior-eye observation camera 656 is adjusted so as to be aligned with the optical axis of the measurement optical system. The alignment in the X-Y position can be performed by observing the anterior eye of the subject eye 607 on the monitor.

The focus of the anterior-eye observation camera 656 is adjusted to come into focus on the iris of the subject eye 607 when it becomes equal to the working distance of the measurement optical system. This allows alignment in the Z position by observing the iris on the monitor. The anterior-eye illuminating light source is a light emitting diode (LED) with a wavelength of 970 nm. The anterior-eye observation camera 656 is a charge-coupled device (CCD) camera.

Next, a fixation-lamp optical system will be described. The fixation-lamp optical system includes a dichroic mirror 658-2 and a fixation-lamp panel 657. The dichroic mirror 658-2 reflects visible light from the fixation-lamp panel 657 and transmits the measurement light 606 and the return light 608. This allows a pattern displayed on the fixation-lamp panel 657 to be projected to the retina of the subject eye 607 via the dichroic mirror 658-2. Displaying a desired pattern on the fixation-lamp panel 657 allows designating the direction of fixation of the subject eye 607 to allow setting the range of the retina to be imaged. The fixation-lamp panel 657 is an organic electroluminescence (EL) panel.

Procedure of Tomographic Imaging

Figure 2:
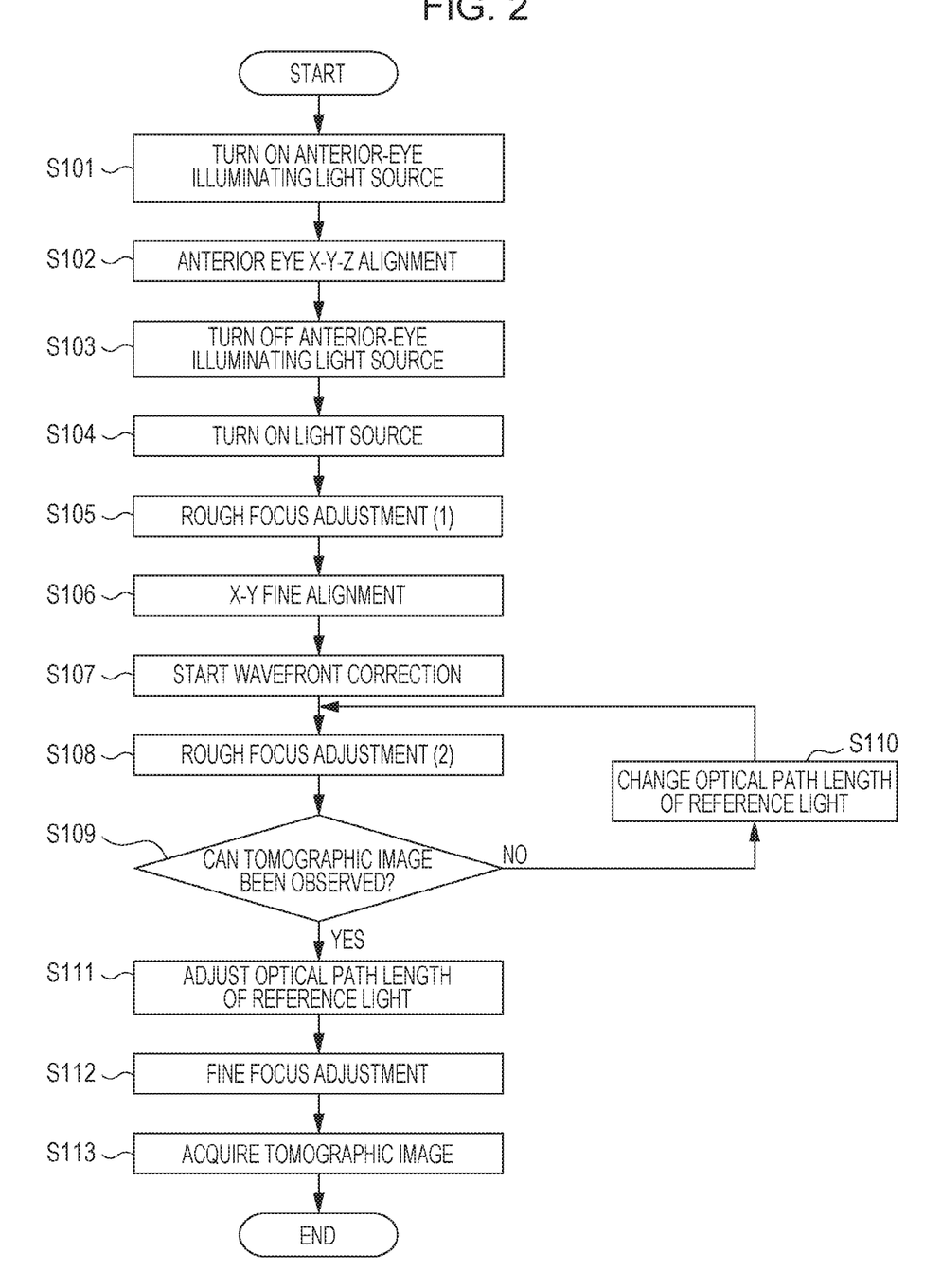
FIG. 2 is a flowchart illustrating the imaging procedure of the tomographic-image acquisition system according to the first embodiment of the present invention.

Referring next to the flowchart of FIG. 2, a procedure for acquiring tomographic images of the eye fundus using the fundus-image acquisition system 500 of the present embodiment will be described.

First, the user presses an anterior-eye illuminating light source button (not illustrated) displayed on the monitor of the personal computer 625, with the subject eye 607 of the subject disposed at a predetermined position of the fundus-image acquisition system 500, to turn on the anterior-eye illuminating light source (step S101). When the anterior-eye illuminating light source is turned on, the anterior eye part of the subject eye 607 photographed by the anterior-eye observation camera 656 is displayed on the monitor.

When the anterior-eye illuminating light source is turned on, the user performs anterior eye X-Y-Z alignment while observing the anterior eye part displayed on the monitor (step S102). Since the X-Y-Z position of the anterior-eye observation camera 656 has been adjusted, as described above, the X-Y-Z position of the apparatus is adjusted so that the X-Y position and the focus (Z) of the anterior eye part displayed on the monitor are aligned.

After completion of the alignment, the user presses the anterior-eye illuminating light source button again to turn off the anterior-eye illuminating light source (step S103), and the user presses a light source button (not illustrated) displayed on the monitor to turn on the light source 601 (step S104).

When the light source 601 is turned on, the user gives an instruction for rough focus adjustment while viewing a Hartmann image from the wavefront sensor 655 displayed on the monitor (step S105). In response to the user moving a focus adjusting bar (not illustrated) displayed on the monitor, the electrically driven stage 617-2 moves so that the focus of the measurement light 606 is adjusted. Here, the focus instruction is given so as to reduce vignetting due to the return light 608 incident on the wavefront sensor 655 in the measurement optical system as much as possible (focus adjustment).

At that time, the personal computer 625 adjusts the optical path length of the reference light 605 by moving the electrically driven stage 617-1 according to the amount of adjustment (change amount) of the optical path length of the measurement light 606 with the movement of the electrically driven stage 617-2.

The relationship between the amount of adjustment of the optical path length of the measurement light 606 and the amount of movement of the electrically driven stage 617-2 for adjusting the optical path length of the reference light 605 will be described. In the present embodiment, the reference light 605 reflected by the mirror 614-3 is then reflected by the mirror 614-15 to return to the mirror 614-3 again. In this configuration, when the electrically driven stage 617-1 is moved by Δ, the optical path length of the reference light 605 changes by 2Δ.

Meanwhile, the measurement light 606 is reflected by the mirror 614-10 and is then reflected by the mirrors 614-11 to 614-12 to go to the mirror 614-13. The return light 608 is reflected by the mirror 614-13 and is thereafter reflected by the mirrors 614-11 to 614-12 to go back to the mirror 614-10 again. In this configuration, when the electrically driven stage 617-2 is moved by Δ', the optical path length of the measurement light 606 changes by 4Δ'.

Accordingly, in this case, the electrically driven stage 617-1 is moved by twice the amount of movement of the electrically driven stage 617-2 (corresponding to the adjustment amount of the optical path length) by the focus adjustment responding to the focus instruction ($\Delta=2\Delta'$). This allows performing focus adjustment without changing the display position of the tomographic image in the depth direction.

The movable range of the electrically driven stage 617-1 is set at 350 mm, and the movable range of the electrically driven stage 617-2 is set at 160 mm, as described above. The reason the movable range of the electrically driven stage 617-1 is set longer than twice the movable range of the electrically driven stage 617-2 is to cope with the adjustment amount of the optical path length depending on the individual differences of the axial length of the subject eye 607, in addition to the adjustment amount of the optical path length of the measurement light 606 by the focus adjustment. For the individual differences of the eye axial length, a movable range of 30 mm (±15 mm) is set. When the electrically driven stage 617-1 of the optical-path-length adjusting unit is moved in conjunction with the focus adjustment, it is only required that the electrically driven stage 617-1 is adjusted within 30 mm, of the entire movable range of 350 mm, at the optical length adjustment describe below (step S110). Thus, the adjustment range can be small, reducing the time required for adjustment, thereby simplifying the adjustment.

When a Hartmann image from the wavefront sensor 655 can be observed on the monitor by rough focus adjustment, the user then performs X-Y fine alignment while viewing the position of the Hartmann image (step S106). The center position of the wavefront sensor 655 is adjusted so as to be aligned with the optical axis of the measurement optical system. Therefore the position of the subject eye 607 is adjusted according to a user instruction so that the Hartmann image is aligned with the center of the wavefront sensor 655.

After completion of the X-Y alignment, the user presses a wavefront correction button (not illustrated) displayed on the monitor to start wavefront correction using the deformable mirror 659 (step S107). The personal computer 625 deforms the deformable mirror 659 based on the aberration measured by the wavefront sensor 655 to correct the aberration of the subject eye 607.

After completion of the wavefront correction, the user performs rough focus adjustment of the measurement light 606 again while viewing the tomographic image (step S108). Here, the focus of the measurement light 606 is adjusted in response to the user moving the focus adjusting bar displayed on the monitor, as at step S105. The personal computer 625 moves the electrically driven stage 617-1 according to the amount of adjustment of the optical path length of the measurement light 606 by the movement of the electrically driven stage 617-2 to adjust the optical path length of the reference light 605.

At that time, the user observes the tomographic image on a tomographic-image display area (not illustrated) on the monitor while adjusting the focus of the measurement light 606 (step S109). However, there is a possibility that the tomographic images cannot be observed even if the focus adjustment is performed. This occurs when the difference in optical path length between the measurement light 606 and the reference light 605 is large, so that the tomographic image is out of the tomographic-image display area. In this case, the user gives an instruction for the optical path length by moving an optical-path-length adjustment bar (not illustrated) displayed on the monitor to change the optical path length of the reference light 605 as appropriate (step S110). When the tomographic image can be observed, the processing returns to the rough focus adjustment (step S108) to perform adjustment.

Whether the tomographic image is displayed in the tomographic-image display area may be determined using a known technique, for example, by determining whether the luminance values of vertical lines corresponding to an A scan line in the area include luminance values equal to or greater than a predetermined value.

The change in the optical path length of the reference light 605 (the instruction for the optical path length) at step S110 is performed within the movable range of 30 mm (±15 mm) of the electrically driven stage 617-1. This optical path length change (step S110) and the rough focus adjustment (step S108) are repeated until a tomographic image is observed in the tomographic-image display area.

After a tomographic image is observed, the optical path length of the reference light 605 is adjusted (step S111). Here, the optical path length of the reference light 605 is adjusted in response the user moving the optical-path-length adjustment bar again so that the display position of the tomographic image is aligned to a desired location in the tomographic-image display area. At that time, the personal computer 625 does not perform control to move the electrically driven stage 617-2 according to the adjustment amount of the optical path length of the reference light 605 by the movement of the electrically driven stage 617-1. This allows adjusting only the depthwise display position of the tomographic image while maintaining the focus state obtained at step S108.

When the tomographic image is adjusted to a desired display position, fine focus adjustment of the measurement light 606 is performed by the user moving the focus adjusting bar displayed on the monitor (step S112). It is difficult for an adaptive optics OCT apparatus with high lateral resolution to attain focus over the entire depthwise area of the retina at the same time because the numerical aperture (NA) for the measurement light 606 at the eye fundus is large and the focal depth is small. For this reason, the fine focus adjustment is performed so that the measurement light 606 is focused on a target layer.

For example, for a photoreceptor inner segment/outer segment junction zone (ellipsoid zone), the focus is adjusted so as to maximize the luminance of the zone. Here, as at step S105, the personal computer 625 adjusts the optical path length of the reference light 605 by moving the electrically driven stage 617-1 according to the adjustment amount of the optical path length of the measurement light 606 with the movement of the electrically driven stage 617-2. This allows adjusting only the focal position while maintaining the depthwise display position of the tomographic image adjusted at step S111.

After the measurement light 606 is adjusted to the desired focus state by the fine focus adjustment, the user presses a imaging button (not illustrated) displayed on the monitor to acquire a tomographic image (step S113). The interfered light of the measurement light 606 and the reference light 605 is received by the line camera 639, where the interfered light is converted to voltage signals. The obtained voltage signals are converted to digital values, and the data is stored and processed by the personal computer 625.

In the present embodiment, by adjusting the optical path length of the reference light 605 according to the adjustment amount of the optical path length at the focus adjustment of the measurement light 606, the time required for focus adjustment and display position adjustment of the tomographic image is reduced, thereby simplifying the adjustment.

Second Embodiment

A second embodiment of the present invention will be described in detail below with reference to the drawings.

Apparatus Configuration

Figure 3:
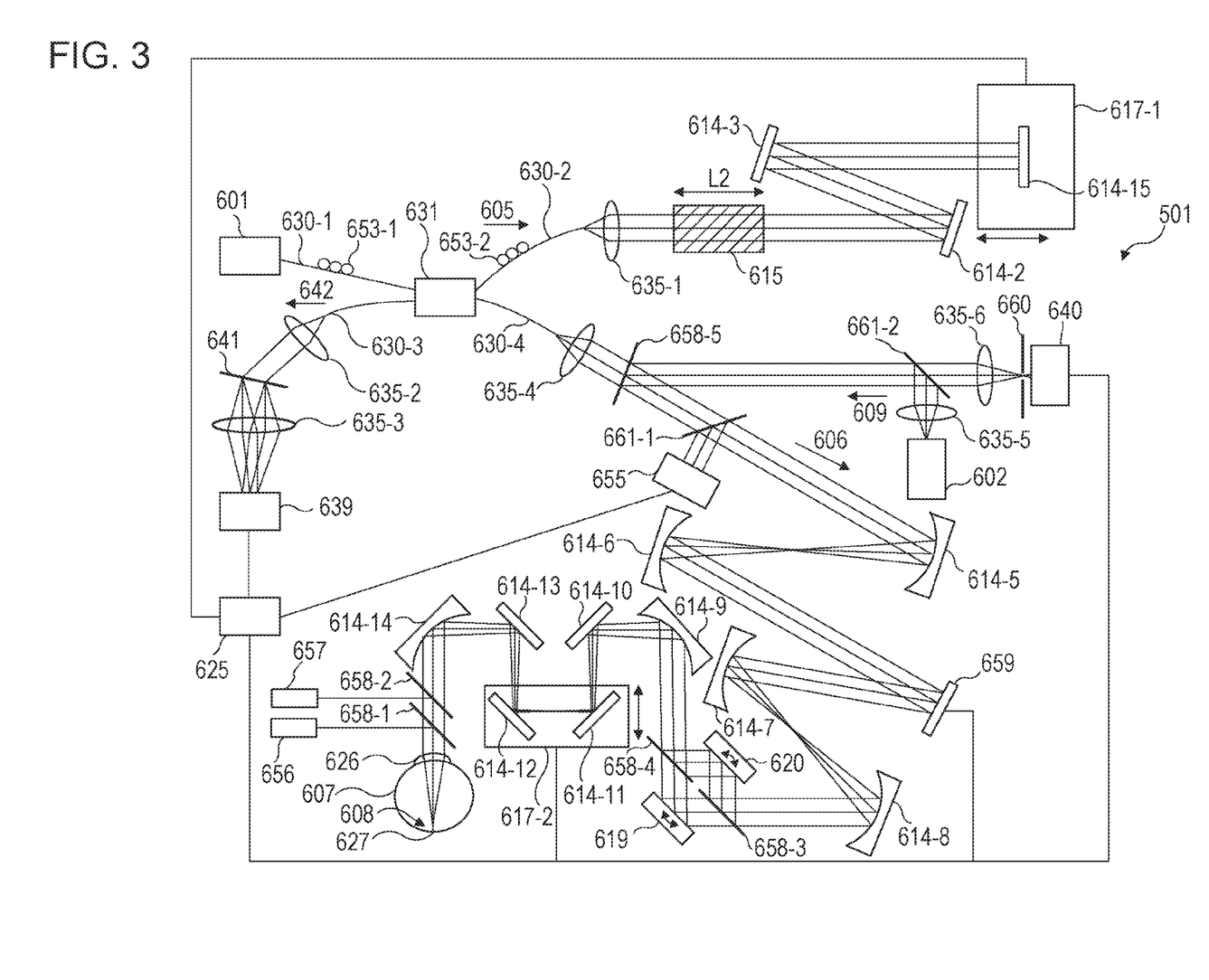
FIG. 3 is a schematic diagram illustrating the configuration of a tomographic-image acquisition system according to a second embodiment of the present invention.

A tomographic-image acquisition system 501, which is a form of an optical interference tomographic-image acquisition system according to the present embodiment, will be described with reference to FIG. 3. The basic configuration of the image acquisition system 501 is similar to the configuration of the fundus-image acquisition system 500 according to the first embodiment. However, the image acquisition system 501 differs from the fundus-image acquisition system 500 in that a scanning laser ophthalmoscope (SLO) for observing the eye fundus of the subject eye 607 is added.

A light source 602 in the present embodiment is a light source for emitting light with a different wavelength from that of the light source 601. The light source 602 is an SLD with a wavelength of 780 nm. Although the kind of the light source here is the SLD, a laser diode (LD) or another light source may be used.

The light emitted from the light source 602 is guided to a lens 635-5, where the light is adjusted to parallel light with a beam diameter of 4 mm. The light that has passed through the lens 635-5 is guided to a beam splitter 661-2, where the light is separated to transmitted light and reflected light (observation light 609) at an intensity ratio of 90 to 10. The observation light 609 reflected by the beam splitter 661-2 goes to a dichroic mirror 658-5. The dichroic mirror 658-5 transmits light with the wavelength of the light source 601 and reflects light with the wavelength of the light source 602. The observation light 609 reflected by the dichroic mirror 658-5 passes through an optical path common to the measurement light 606 via a beam splitter 661-1, mirrors 614-5 to 614-6, a deformable mirror 659, and a mirror 614-7 and is reflected by a mirror 614-8. Dichroic mirrors 658-3 to 658-4 transmit light with the wavelength of the light source 601 and reflects light with the wavelength of the light source 602.

Thus, the observation light 609 reflected by the mirror 614-8 is reflected by the dichroic mirror 658-3 onto the mirror of an X-Y scanner 620. Although the X-Y scanner 620 here includes one mirror for the sake of clarity, the X-Y scanner 620 actually includes two mirrors for X scanning and Y scanning disposed close to each other and raster-scans the retina 627 in a direction perpendicular to the optical axis. The observation light 609 is adjusted so that the center is aligned with the rotation center of the mirrors of the X-Y scanner 620.

The measurement light 606 and the observation light 609 are separated from each other by the dichroic mirror 658-3 so that the X-Y scanner 619 for the measurement light 606 and the X-Y scanner 620 for the observation light 609 are separately disposed. This allows separate scanning of the measurement light 606 and the observation light 609, allowing independent setting of the imaging range and the observation range.

Although the scanning speed of the measurement light 606 is limited by the reading speed of the line camera 639, providing the separate X-Y scanners allows increasing the scanning speed of the observation light 609, thereby increasing the frame rate of acquisition of eye fundus front images.

This is advantageous, for example, in improving the accuracy of detecting the motion of the subject eye 607 from the eye fundus front images to perform position correction (tracking) of the image acquisition or the like. In the present embodiment, a Galvano mirror is used for the X-Y scanner 619 for the measurement light 606, a resonant mirror is used for the X-scanner for the observation light 609, and a Galvano mirror is used for the Y-scanner for the observation light 609.

The observation light 609 reflected by the X-Y scanner 620 is reflected by the dichroic mirror 658-4 and is applied to the subject eye 607 through an optical path common to the measurement light 606. The observation light 609 reflected by the eye fundus 627 goes back through the optical path, is reflected by the dichroic mirror 658-5, and passes through the beam splitter 661-2. The intensity ratio of the transmitted light (observation light 609) to the reflected light is 90 to 10. The observation light 609 that has passed through the beam splitter 661-2 is collected by the lens 635-6 and passes through a pinhole plate 660. The pinhole plate 660 is adjusted to a position conjugate to the eye fundus and acts as a confocal diaphragm that blocks unwanted light coming from other than the conjugate point.

Thus, the lens 635-5 to the mirror 614-14, the lens 635-6, and the pinhole plate 660 constitute the observation optical system in the present embodiment.

The observation light 609 that has passed through the pinhole is received by a light receiving element 640. An avalanched photo diode (APD) is used for the light receiving element 640. The intensity of the light received by the APD is converted to a voltage signal. The obtained voltage signals are converted to digital values, which are processed by the personal computer 625 to form an eye fundus front image. The formed eye fundus front image is displayed on the monitor of the personal computer 625.

Part of the return light 608 produced by the beam splitter 661-1 enters the wavefront sensor 655, where the aberration of the return light 608 is measured. In the present embodiment, the beam splitter 661-1 reflects part of the return light 608 and transmits the observation light 609. This allows selective measurement of the aberration of the return light 608.

Procedure for Tomographic Imaging

Figure 4:
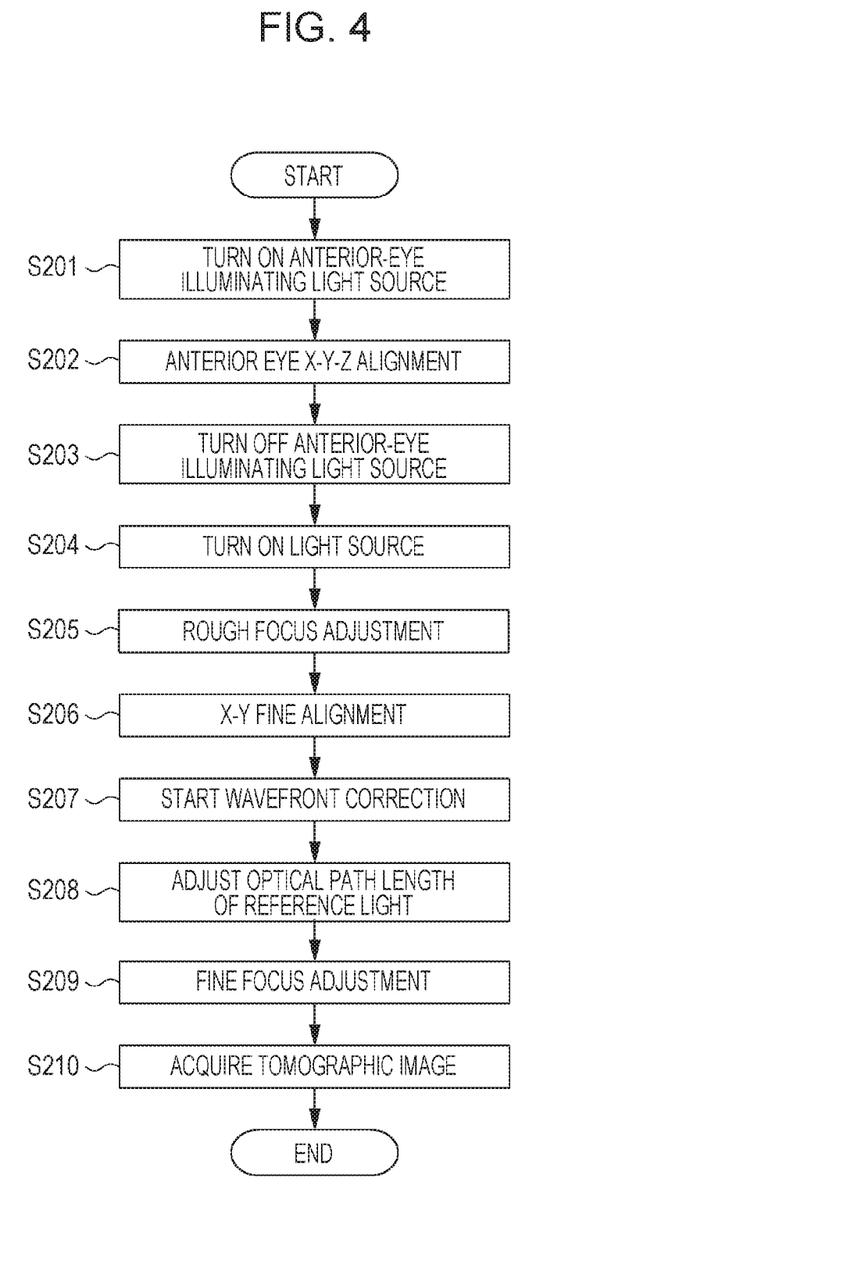
FIG. 4 is a flowchart illustrating the imaging procedure of the tomographic-image acquisition system according to the second embodiment of the present invention.

Referring next to the flowchart of FIG. 4, a procedure for acquiring tomographic images of the eye fundus of the subject eye 607 using the fundus-image acquisition system 501 of the present embodiment will be described.

First, at steps S201 to S203, alignment of the anterior eye part is performed as at steps S101 to S103 of the first embodiment.

After completion of the alignment, the user presses a light source button (not illustrated) displayed on the monitor to turn on the light source 601 and the light source 602 (step S204). The timing when the light source 601 is turned on is not limited to the above timing. For example, it may be after the rough focus adjustment at step S205 or after the X-Y fine alignment at step S206.

When the light source 602 is turned on, the user performs rough focus adjustment while viewing an eye fundus front image acquired in the observation optical system (step S205). When the user moves a focus adjusting bar (not illustrated) displayed on the monitor, the electrically driven stage 617-2 moves. The electrically driven stage 617-2 and the mirrors 614-11 to 614-12 are disposed on an optical path common to the measurement light 606 and the observation light 609, so that, as focus adjustment of the observation light 609 is performed, rough focus adjustment of the measurement light 606 is also performed in conjunction therewith. The focus adjustment here is performed so that the luminance of the eye fundus front image becomes maximum.

Here, the personal computer 625 adjusts the optical path length of the reference light 605 by moving the electrically driven stage 617-1 according to the adjustment amount of the optical path length of the measurement light 606 with the movement of the electrically driven stage 617-2.

At that time, the electrically driven stage 617-1 is moved by twice the amount of movement of the electrically driven stage 617-2 by the focus adjustment ($\Delta=2\Delta'$), as in the first embodiment. This allows performing focus adjustment without changing the display position of the tomographic image in the depth direction.

When the luminance of the eye fundus front image becomes maximum by the rough focus adjustment, X-Y fine alignment is performed as in the first embodiment (step S206), and wavefront correction using the deformable mirror 659 is started (step S207).

Upon completion of the wavefront correction, the user moves an optical-path-length adjustment bar (not illustrated) displayed on the monitor to adjust the optical path length of the reference light 605 (step S208). Here, the user adjusts the optical path length so that the display position of the tomographic image comes to a desired position in the tomographic-image display area. At that time, the personal computer 625 does not perform control to move the electrically driven stage 617-2 according to the adjustment amount of the optical path length of the reference light 605 by the movement of the electrically driven stage 617-1. This allows adjusting only the depthwise display position of the tomographic image while maintaining the focus state obtained at step S205. The adjustment of the optical path length of the reference light 605 at step S208 is performed within the moving range of 30 mm (±15 mm) of the electrically driven stage 617-1, which is an adjustment range for the individual differences of the eye axis length.

After the tomographic image is adjusted to the desired display position, fine focus adjustment of the measurement light 606 is performed as in the first embodiment (step S209).

Here, as at step S205, the personal computer 625 adjusts the optical path length of the reference light 605 by moving the electrically driven stage 617-1 according to the adjustment amount of the optical path length of the measurement light 606 with the movement of the electrically driven stage 617-2. This allows adjusting only the focal position while maintaining the depthwise display position of the tomographic image adjusted at step S208.

After the measurement light 606 is adjusted to a desired focus state by the fine focus adjustment, the user presses a imaging button (not illustrated) displayed on the monitor to acquire a tomographic image (step S210). The interfered light of the measurement light 606 and the reference light 605 is received by the line camera 639, where the interfered light is converted to voltage signals. The obtained voltage signals are converted to digital values, and the data is stored and processed by the personal computer 625.

In the present embodiment, by adding the observation optical system to the first embodiment and performing the focus adjustment of the observation light 609 and the focus adjustment of the measurement light 606 in conjunction, the time required for the rough focus adjustment of the measurement light 606 can be reduced, simplifying the adjustment.

Third Embodiment

A third embodiment of the present invention will be described in detail below with reference to the drawings.

Apparatus Configuration

Figure 5:
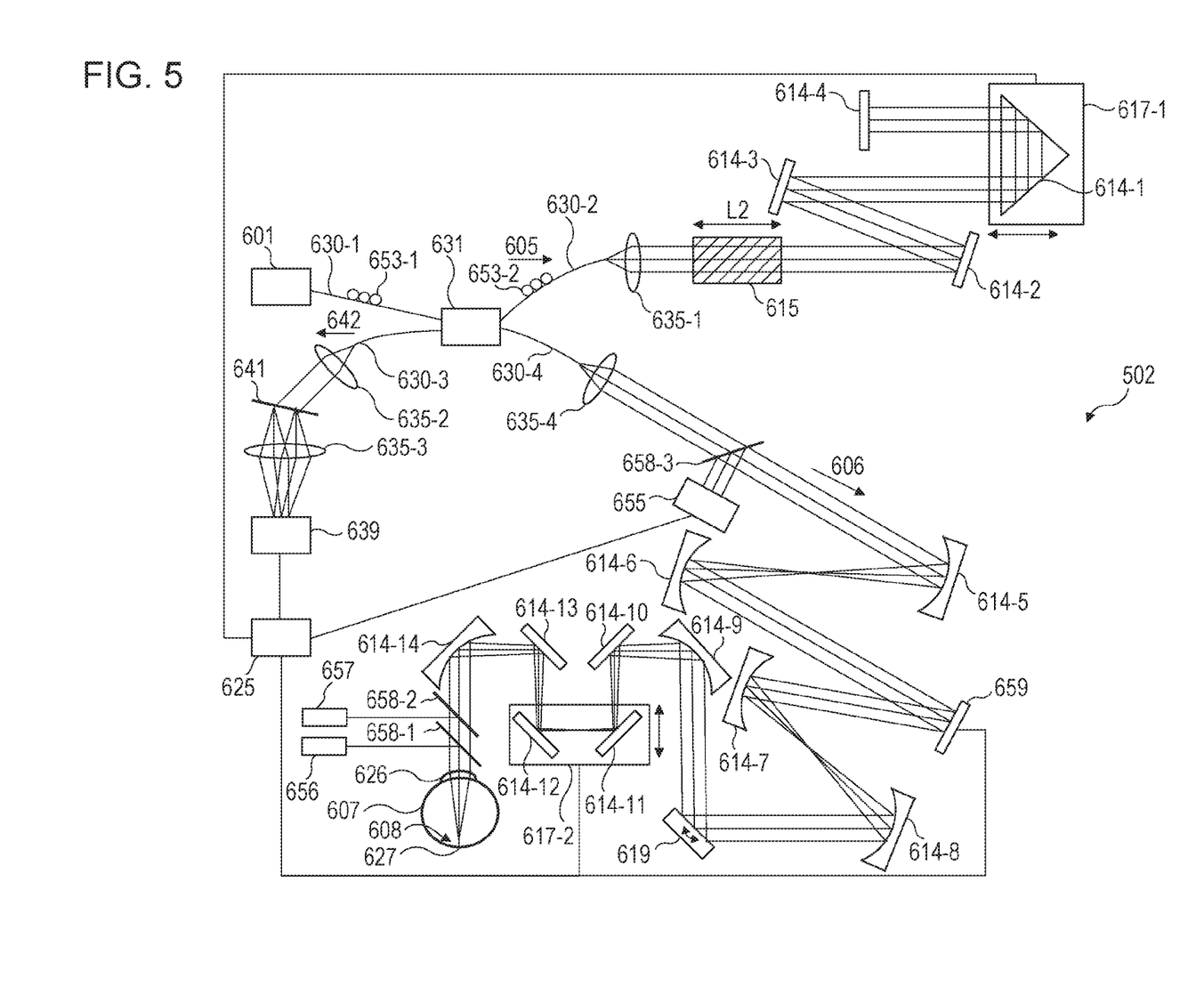
FIG. 5 is a schematic diagram illustrating the configuration of a tomographic-image acquisition system according to a third embodiment of the present invention.

A tomographic-image acquisition system 502, which is a form of an optical interference tomographic-image acquisition system according to the present embodiment, will be described with reference to FIG. 5. The basic configuration of the image acquisition system 502 is similar to the configuration of the fundus-image acquisition system 500 according to the first embodiment. However, the third embodiment differs from the first embodiment in that mirrors 614-1 and 614-4 are used instead of the mirror 614-15 disposed in the reference optical path.

The optical path of the reference light 605 in the present embodiment will be described. The reference light 605 produced by divided the light with an optical coupler 631 is guided to a lens 635-1 through a single mode fiber 630-2 and is adjusted to parallel light with a beam diameter of 2 mm. Next, the reference light 605 is guided to the mirror 614-1 serving as a reference mirror by mirrors 614-2 to 614-3. Here, a retroreflector is used as the reference mirror. The light that has exited from the mirror 614-1 is reflected by the mirror 614-4 and is then reflected by the mirror 614-1, the mirror 614-3, and the mirror 614-2 in sequence into the optical coupler 631 again.

The mirror 614-1 is mounted on an electrically driven stage 617-1 and constitutes an optical-path-length adjusting unit in the present embodiment. The electrically driven stage 617-1 can move in the direction indicated by the arrow to adjust the optical path length of the reference light 605. Here, the movable range of the electrically driven stage 617-1 is set at 175 mm. The electrically driven stage 617-1 is controlled by a personal computer 625 serving as a control unit in the present embodiment.

In the present embodiment, the reference light 605 reflected by the mirror 614-3 is reflected by the mirror 614-1 to go to the mirror 614-4. The reference light 605 reflected by the mirror 614-4 is reflected by the mirror 614-1 to return to the mirror 614-3. In this configuration, when the electrically driven stage 617-1 is moved by $\Delta$, the optical path length of the reference light 605 changes by $4\Delta$.

Meanwhile, when the electrically driven stage 617-2 of the measurement optical system is moved by $\Delta'$ as in the first embodiment, the optical path length of the measurement light 606 changes by $4\Delta'$.

Thus, moving the electrically driven stage 617-1 by the same moving amount ($\Delta=\Delta'$) as the moving amount of the electrically driven stage 617-2 by focus adjustment allows performing focus adjustment without changing the depthwise display position of the tomographic image.

As described above, the movable range of the electrically driven stage 617-1 is set at 175 mm, and the movable range of the electrically driven stage 617-2 is set at 160 mm, as in the first embodiment. The reason why the movable range of the electrically driven stage 617-1 is set longer than the movable range of the electrically driven stage 617-2 is to cope with the adjustment amount of the optical path length depending on the individual differences in eye axial length, in addition to the adjustment amount of the optical path length of the measurement light 606 by the focus adjustment. For the individual differences in axial length, a movable range of 15 mm (±7.5 mm) is set.

In the present embodiment, the movable range of the electrically driven stage 617-1 can be smaller than that of the first embodiment. This reduces a space for moving the electrically driven stage 617-1, which is advantageous in reducing the size of the apparatus.

Furthermore, since the amount of movement of the electrically driven stage 617-1 and the amount of movement of the electrically driven stage 617-2 are the same, the electrically driven stages 617-1 and 617-2 may be constituted by one electrically driven stage. In this case, an electrically driven stage on which only the mirror 614-1 is mounted is disposed on the one electrically driven stage. By changing only the optical path length of the reference light 605 using this electrically driven stage, the individual differences of the eye axial length can be coped with. The movable range of the electrically driven stage may be no more than 15 mm. This allows using a smaller stage, which is advantageous in reducing the size of the apparatus.

Modification of Embodiments

Having described preferred embodiments of the present invention, it is to be understood that the present invention is not limited to the embodiments and that various modifications and changes can be made within the spirit and scope of the invention.

Figure 6:
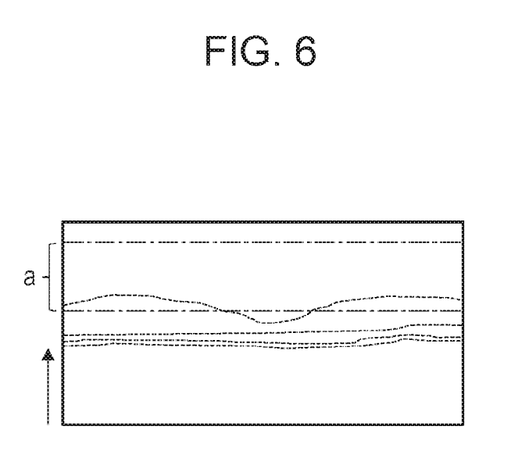
FIG. 6 is a schematic diagram illustrating a tomographic-image display area according to another embodiment of the present invention.

In the first to third embodiments, the optical path length of the reference light 605 is adjusted at focus adjustment always in conjunction with the adjustment of the optical path length of the measurement light 606 by the focus adjustment. However, when the tomographic image comes close to a desired depthwise display position because of the change in the optical path length of the measurement light 606 along with the focus adjustment, the operative association is not needed. FIG. 6 illustrates a tomographic-image display area displayed on the monitor, in which the broken lines schematically indicate a tomographic image of the retina of the eye fundus of the subject eye. The upper end of the tomographic-image display area is a position where the optical path lengths of the measurement light 606 and the reference light 605 are equal (a coherent gate position). In an OCT apparatus, as the difference in optical path length between the measurement light 606 and the reference light 605 becomes longer, and the tomographic image is separated from the coherence gate position, the interference fringes become higher in frequency and the signal-to-noise (SN) ratio of the image decreases. In contrast, the tomographic image is close to the coherence gate position, the SN ratio of the image is also decreased by the noise of the direct current (DC) component of the interference fringes. For this reason, an area slightly away from the upper end of the tomographic-image display area (an area a indicated by the one-dot chain lines in FIG. 6) is set as a predetermined range. When focus adjustment is performed, the tomographic image is also moved in the vertical direction (depth direction) because of a change in the optical path length of the measurement light 606 along therewith. Here, the integrated luminance value in a specified range is calculated. If the integrated luminance value increases when a predetermined amount of focus adjustment is performed (if the tomographic image moves in the direction of the arrow in FIG. 6), the optical path length of the reference light 605 is not adjusted in conjunction with the focus adjustment. This allows combining the focus adjustment of the measurement light 606 and the display position adjustment of the tomographic image in the depth direction, reducing the time required to adjust the optical path length of the reference light 605. In contrast, if the integrated luminance value decreases when a predetermined amount of focus adjustment is performed (if the tomographic image moves in the direction opposite to the arrow in FIG. 6), the optical path length of the reference light 605 is adjusted in conjunction with the focus adjustment. This prevents an increase in the amount of adjustment of the optical path length of the reference light 605. The predetermined amount of focus adjustment for determining whether the integrated luminance value has increased or decreased may be set as appropriate, for example, to one tenth of the predetermined range of the tomographic image. Here, an integrated luminance value within a predetermined range is used as an index for determining whether to operatively associate with the focus adjustment. However, this is not intended to limit the present invention. For example, the tomographic image may be binarized using a predetermined threshold, and the number of pixels equal to or greater than the predetermined threshold within a predetermined range may be used as the index. The predetermined threshold may be set as appropriate, fro example, from the luminance of an image obtained by imaging a human eye or a model eye in advance.

In the first to third embodiments, the optical path length of the reference light 605 is adjusted by the same amount as the adjustment amount of the optical path length of the measurement light 606 by focus adjustment. However, this is given for mere illustrative purposes. In general, it is known that the eye axial length tends to vary depending on the diopter. Usually, myopic eyes tend to have longer axial length, and far-sighted eyes tend to have shorter axial length. For this reason, the adjustment of the optical path length of the reference light 605 operatively associated with focus adjustment may be performed in consideration of a predetermined offset amount depending on the diopter. The amount of offset can be determined, for example, by measuring the axial lengths of the subject eyes with various diopters and fitting the measured values using a numerical expression. The offset amount is stored in the personal computer 625, and the amount of movement of the stage 617-1 is controlled by adding the stored offset amount to the adjustment amount of the optical path length of the measurement light 606 at focus adjustment. This may increase the possibility of decreasing the adjustment amount of the optical path length of the reference light 605 after rough focus adjustment, further reducing the time required to adjust the optical path length of the reference light 605, which is advantageous in further simplifying the adjustment.

In the first to third embodiments, the fine focus adjustment at step S112 and step S209 is performed using the focus adjusting unit of the measurement optical system. However, if the aberration of the subject eye 607 is small, so that there is a margin in the stroke of the deformable mirror 659, the deformable mirror 659 may be used. In this case, the fine focus adjustment is performed by deforming the deformable mirror 659. At that time, the optical path length of the measurement light 606 is not changed by the focus adjustment. For this reason, the optical path length of the reference light 605 is not adjusted in conjunction with the focus adjustment. Thus, fine focus adjustment can be performed without changing the depthwise display position of the tomographic image.

Although, in the second embodiment, the focus adjustment of the measurement light 606 and the observation light 609 is performed using the common optical system, the focus adjustment may be performed using separate optical systems. In this case, the measurement light 606 and the observation light 609 are separated from each other between the focus adjusting unit for the measurement light 606 and the subject eye 607, mirrors for focus adjustment are disposed in each of the optical path of the measurement light 606 and the optical path of the observation light 609, and the mirrors are moved in conjunction to perform focus adjustment. In this case, the positions of the mirrors for focus adjustment corresponding to the individual diopters are measured in advance by simulation or with a tool or the like, and the positional data is stored in the personal computer 625. Then, the mirrors for focus adjustment of the measurement light 606 are moved by the amount of movement stored in the personal computer 625 in conjunction with the movement of the mirrors by the focus adjustment of the observation light 609. Thus, the focus adjustment of the measurement light 606 can be performed in conjunction with the focus adjustment of the observation light 609, reducing the time required for rough focus adjustment, which further simplifies the adjustment. In this case, the optical system for the focus adjustment of the observation light 609 may not be the plurality of mirrors serving as reflection members but may be a plurality of lenses. This eliminates the need to separate the incident light and the reflected light from each other, which is necessary for the reflection optical system. This is advantageous in reducing the size of the optical system. The separation of the optical paths of the measurement light 606 and the observation light 609 from each other prevents unwanted light from entering the wavefront sensor. This allows the aberration of the measurement light 606 to be accurately measured and corrected. Thus, a tomographic image with high lateral resolution can be acquired.

Other Embodiments

In the above embodiments, a spectral domain OCT is used which uses a broadband light source that generates broadband light to be applied to the subject eye 607. This is not intended to limit the present invention. For example, a wavelength swept OCT may be used which uses a light source that generates wavelength swept light.

In the above embodiments, the subject is the eye. However, the present invention can also be applied to skin, organs, or other subjects other than the eye. In this case, the present invention has the form of a medical instrument other than the ophthalmic imaging apparatus, for example, an endoscope. Accordingly, the present invention may be an image acquisition apparatus exemplified by an ophthalmic imaging apparatus, and the subject eye may be a form of the subject.

Embodiments of the present invention can also be realized by the following configuration. The above-described embodiments of the present invention can also be realized by a system or apparatus provided with a recording medium (or a storage medium) storing program codes (computer programs) of software for implementing the functions of the embodiments. The recording medium may be a computer-readable recording medium. The computer (or a central processing unit (CPU) or a micro processing unit (MPU)) of the system or apparatus reads and executes the program codes stored in the recording medium. In this case, the program codes read from the recording medium achieves the functions of the embodiments, and the recording medium storing the program codes constitutes the present invention. The embodiments can also be implemented by an application specific integrated circuit (ASIC)) for performing one or more functions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image acquisition apparatus comprising:
   a light source configured to emit light;
   a dividing unit configured to divide the light from the light source into reference light and measurement light;
   an image forming unit configured to form a tomographic image of a subject based on interfered light in which return light from the subject irradiated with the measurement light and the reference light are interfered;
   a focus adjusting unit configured to adjust a focus of the measurement light;
   an optical-path-length adjusting unit configured to adjust an optical path length of the reference light;
   a control unit configured to adjust the optical path length of the reference light by controlling the optical-path-length adjusting unit according a change in an optical path length of the measurement light caused by adjustment of the focus using the focus adjusting unit;
   a display control unit configured to display the formed tomographic image in an image display area of a display unit; and
   a determination unit configured to determine whether a predetermined image in the formed tomographic image comes to a predetermined position in the image display area according to the focus adjustment of the measurement light by the focus adjusting unit,
   wherein, when the predetermined image in the tomographic image is separated from the predetermined position in the image display area by the adjustment of the focus, the control unit executes control of the optical-path-length adjusting unit based on the adjustment of the optical path length of the measurement light, and when the predetermined image in the tomographic image comes to the predetermined position in the image display area by the adjustment of the focus, the control unit does not execute control of the optical-path-length adjusting unit based on the adjustment of the optical path length of the measurement light.

2. The image acquisition apparatus according to claim 1, wherein the control unit controls the optical-path-length adjusting unit so as to adjust the optical path length of the reference light according to an amount of the change in the optical path length of the measurement light caused by the adjustment of the focus.

3. The image acquisition apparatus according to claim 1, further comprising:
   an observation optical system configured to observe the subject by applying observation light whose focus is adjusted to the subject,
   wherein the control unit controls the focus adjusting unit by the focus adjustment of the observation optical system.

4. The image acquisition apparatus according to claim 3, wherein the focus adjusting unit is disposed on an optical path common to a measurement optical system and the observation optical system.

5. The image acquisition apparatus according to claim 1,
   wherein the optical-path-length adjusting unit includes a plurality of reflection members,
   wherein the focus adjusting unit includes at least one set of reflection members, and
   wherein the control unit controls the optical-path-length adjusting unit so as to move the plurality of reflection members according to an amount of movement of the at least one set of reflection members.

6. The image acquisition apparatus according to claim 5,
wherein the focus adjusting unit and the optical-path-length adjusting unit are mounted on a first stage,
wherein the apparatus further includes a second stage mounted on the first stage on which the plurality of reflection members of the optical-path-length adjusting unit are mounted, and
wherein, when the optical-path-length adjusting unit is instructed to adjust the optical path length of the reference light, the optical-path-length adjusting unit adjusts the optical path length of the reference light by moving the second stage.

7. An image acquisition apparatus comprising:
a light source configured to emit light;
a dividing unit configured to divide the light from the light source into reference light and measurement light;
an image forming unit configured to form a tomographic image of a subject based on interfered light in which return light from the subject irradiated with the measurement light and the reference light are interfered;
a focus adjusting unit configured to adjust a focus of the measurement light;
an optical-path-length adjusting unit configured to adjust an optical path length of the reference light;
a focus instruction unit configured to provide an instruction to adjust the focus of the measurement light;
an optical-path-length instruction unit configured to provide an instruction to adjust the optical path length of the reference light; and
a control unit configured, when an instruction to adjust the focus of the measurement light is provided by the focus instruction unit, to control the adjustment using the focus adjusting unit in conjunction with the adjustment using the optical-path-length adjusting unit, and when an instruction to adjust the optical path length of the reference light is provided by the optical-path-length instruction unit, to control the adjustment with the optical-path-length adjusting unit without conjunction with the adjustment with the focus adjusting unit.

8. The image acquisition apparatus according to claim 7, wherein the control unit controls the optical-path-length adjusting unit so as to adjust the optical path length of the reference light according to an amount of adjustment of the optical path length of the measurement light caused by the focus adjustment.

9. The image acquisition apparatus according to claim 7, further comprising:
a display control unit configured to display the formed tomographic image in an image display area of a display unit,
wherein, when a predetermined image in the tomographic image comes to a predetermined position in the image display area by the focus adjustment, the control unit does not control the optical-path-length adjusting unit based on the adjustment of the optical path length of the measurement light.

10. A method for controlling an image acquisition apparatus, the method comprising the steps of:
dividing light from a light source into reference light and measurement light;
controlling adjustment of an optical path length of the reference light according to a change in the measurement light caused by adjustment of a focus of the measurement light in conjunction with each other;
forming a tomographic image of a subject based on interfered light in which return light from the subject irradiated with the measurement light and the reference light are interfered;
displaying the formed tomographic image on an image display area of a display unit; and
determining whether a predetermined image in the formed tomographic image comes to a predetermined position in the image display area according to the focus adjustment to the measurement light in the focus adjusting step,
wherein, in the controlling, when the predetermined image in the tomographic image is separated from the predetermined position in the image display area by the adjustment of the focus, operatively associated control of the optical path length based on the adjustment of the optical path length of the measurement light is executed, and when the predetermined image in the tomographic image comes towards the predetermined position in the image display area by the adjustment of the focus, operatively associated control of the optical path length based on the adjustment of the optical path length of the measurement light is not executed.

* * * * *